US00PP37624P2

(12) United States Plant Patent
Rietberg

(10) Patent No.: US PP37,624 P2
(45) Date of Patent: Aug. 18, 2026

(54) ***HEBE* PLANT NAMED 'Nina'**

(50) Latin Name: ***Hebe* hybrid**
Varietal Denomination: Nina

(71) Applicant: Henrik Christiaan Cozijn Rietberg, Wezep (NL)

(72) Inventor: Henrik Christiaan Cozijn Rietberg, Wezep (NL)

(73) Assignee: EDENS CREATIONS BV, Wezep (NL)

( * ) Notice: Subject to any disclaimer, the term of this patent is extended or adjusted under 35 U.S.C. 154(b) by 0 days.

(21) Appl. No.: 19/385,011

(22) Filed: Nov. 10, 2025

(30) Foreign Application Priority Data

Nov. 19, 2024 (QZ) ..... 20242673

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hebe* plant named 'Nina' that is characterized by its very compact plant habit, its floriferous blooming habit with a long blooming period, its flowers that are intense pink in color, its very small leaf size, and its bright green colored foliage.

3 Drawing Sheets

CROSS REFERENCE TO A RELATED APPLICATION

This application claims priority to European Community Plant Variety Office (CPVO) Plant Breeder's Rights Application No. 2024/2673 filed on Nov. 19, 2024, under 35 U.S.C. 119(f), the entire contents of which is incorporated by reference herein. The information for the Plant Breeders' Rights was received directly from the Inventor.

Botanical classification: *Hebe* hybrid.

Cultivar designation: 'Nina'.

BACKGROUND OF THE INVENTION

The present invention relates to a new and distinct cultivar of *Hebe,* botanically of hybrid origin, known as *Hebe* 'Nina', and will be referred to hereafter by its cultivar name, 'Nina'. 'Nina' is an evergreen shrub grown for use as a container plant and as a landscape shrub.

The new cultivar was derived from a controlled breeding program conducted by the Inventor in Wezep, The Netherlands. The goal of the breeding program was to select a new cultivar of *Hebe* with improved plant health, a very compact plant habit, abundant and long flowering, and bright pink flowers. The new cultivar arose from a cross made in September of 2020 between an unnamed and unpatented proprietary plant from the Inventor's breeding program, reference no. PM20-3003, as the female parent and *Hebe* hybrid 'HOP101' (not patented) as the male parent. The Inventor selected 'Nina' in September of 2021 as a single unique plant amongst the seedlings that resulted from the above cross.

Asexual propagation of the new cultivar was first accomplished by stem cuttings in September of 2021 by the Inventor in Wezep, The Netherlands. Asexual propagation by stem cuttings has determined the characteristics of the new cultivar are stable and reproduced true to type in successive generations.

SUMMARY OF THE INVENTION

The following traits have been repeatedly observed and represent the characteristics of the new cultivar, which in combination distinguish 'Nina' as a new and distinct cultivar of *Hebe.*

1. 'Nina' exhibits a very compact plant habit.
2. 'Nina' exhibits a floriferous blooming habit with a long blooming period.
3. 'Nina' exhibits flowers that are intense pink in color.
4. 'Nina' exhibits a very small leaf size.
5. 'Nina' exhibits bright green colored foliage.

The female parent of 'Nina' differs from 'Nina' in having a more open and less compact plant habit, leaves that are darker green in color, flowers that are lighter pink in color, and a more vigorous growth habit. The male parent of 'Nina' differs from 'Nina' in having leaves that are darker green in color and larger in size, flowers that are blue-purple in color, and a more vigorous growth habit. 'Nina' can be most closely compared to the *Hebe* cultivars 'H14031' (not patented) and 'Nikka' (not patented). 'H14031' is similar to 'Nina' in having foliage that is bright green in color. 'H14031' differs from 'Nina' in having a less compact plant habit, flowers that are less intense pink in color, a shorter flowering period, and in being more sensitive to *Fusarium* sp. 'Nikka' is similar to 'Nina' in having flowers that are pink in color. 'Nikka' differs from 'Nina' in having flowers and leaves that are larger in size and in blooming later in the season.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plantarium, Facebook, Instagram, and Groen-Direkt Boskoop.

BRIEF DESCRIPTION OF THE DRAWINGS

The accompanying color photographs illustrate the overall appearance and distinct characteristics of the new *Hebe*. The photographs were taken of a 7-month-old plant of 'Nina' as grown outdoors in a 10.5-cm container in Wezep, The Netherlands.

The photograph in FIG. 1 provides a side view of a plant of 'Nina' in bloom.

Figure 1:
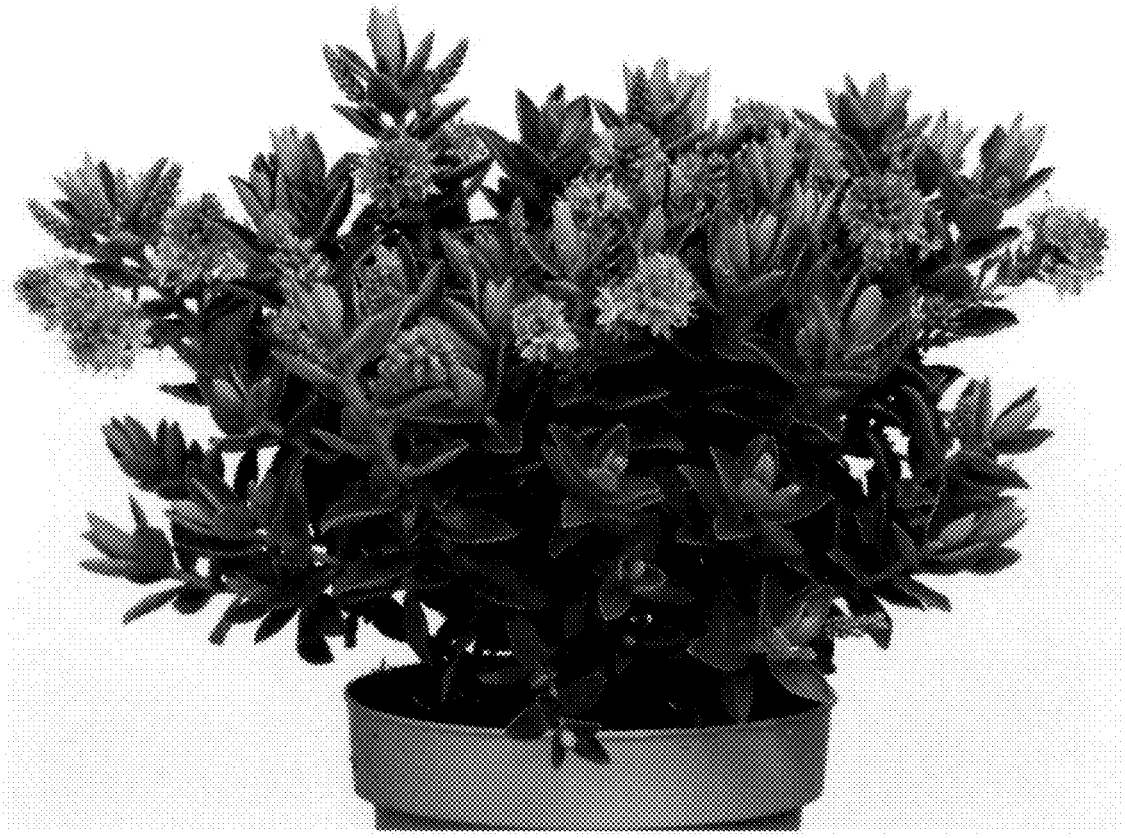
Figure 2:
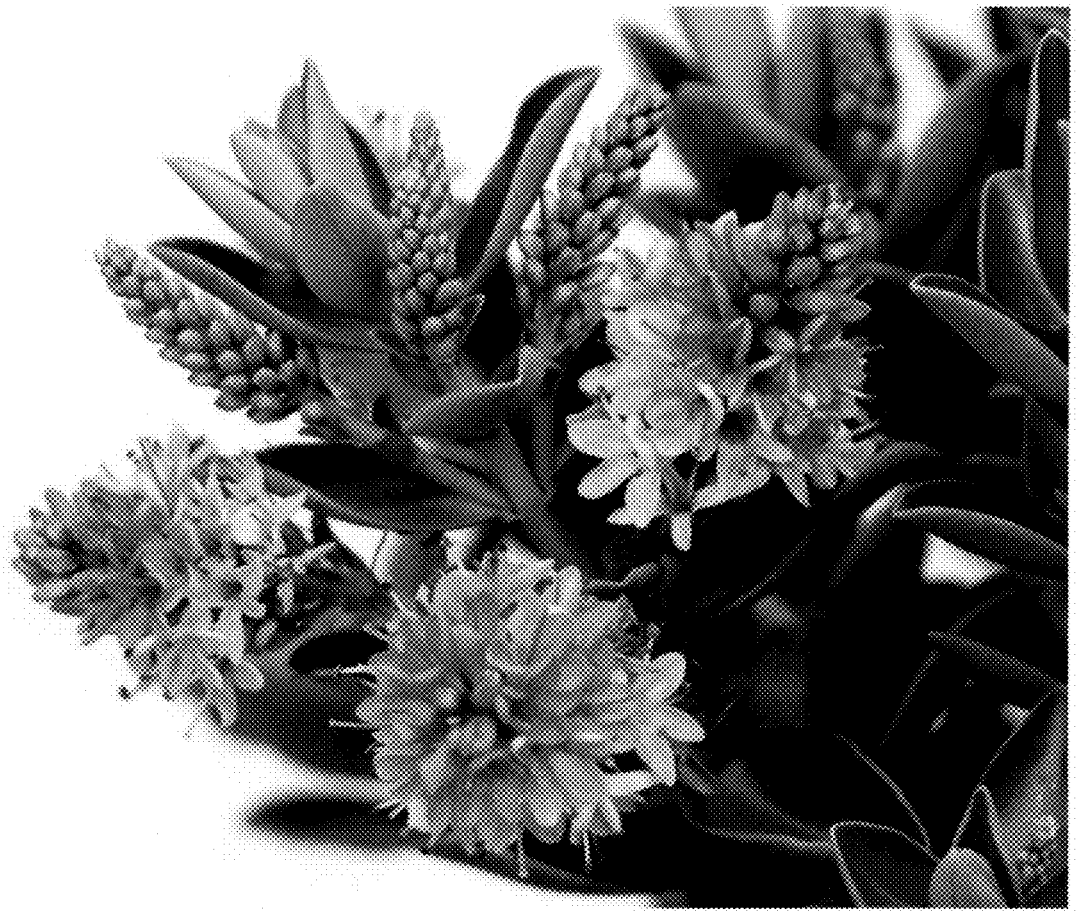

The photograph in FIG. 2 provides a close-up view of the inflorescences of 'Nina'.

Figure 3:
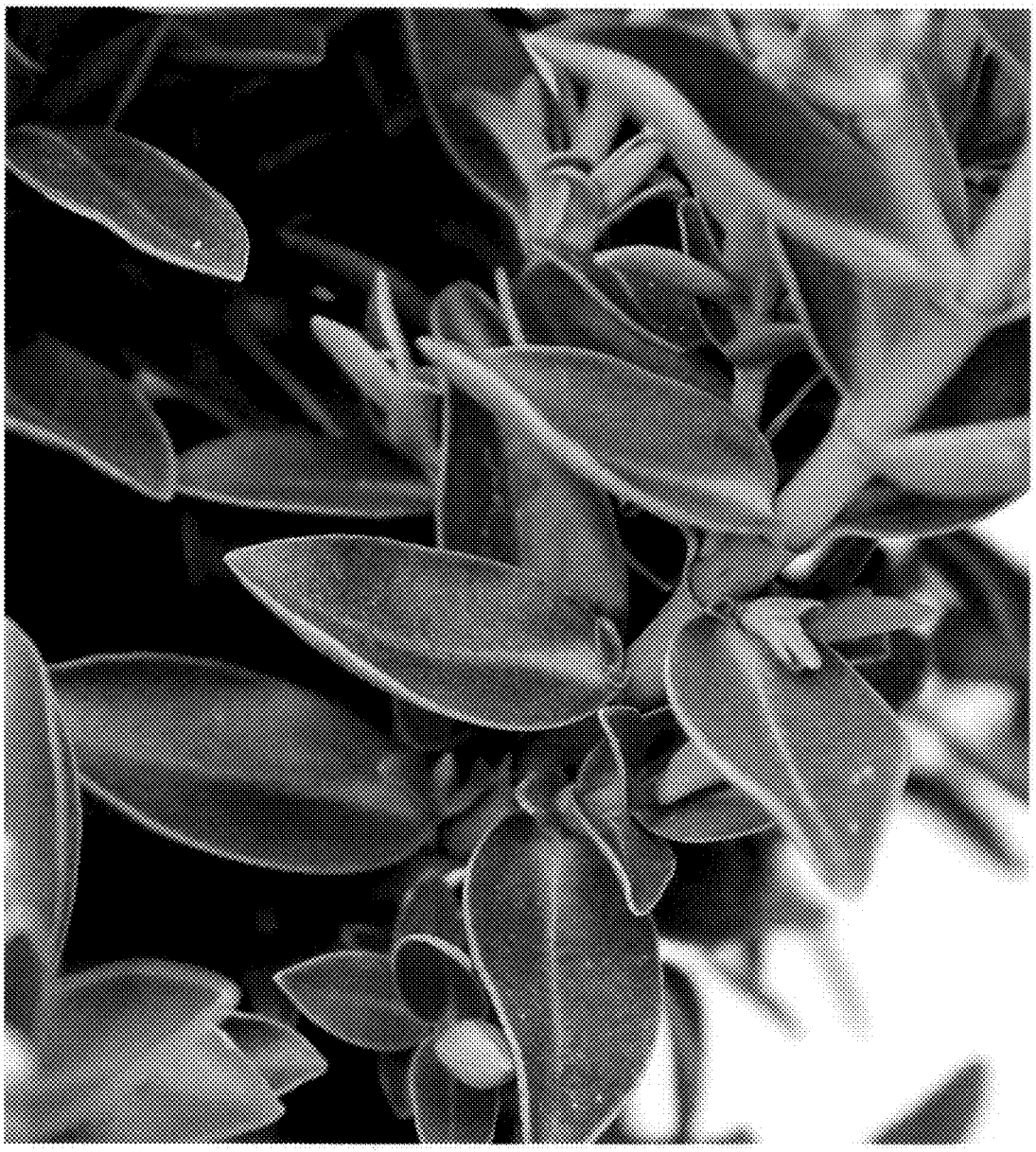

The photograph in FIG. 3 provides a close-up view of the foliage of 'Nina'.

The colors in the photograph may differ slightly from the color values cited in the detailed botanical description, which accurately describe the colors of the new *Hebe*.

DETAILED BOTANICAL DESCRIPTION OF THE PLANT

The following is a detailed description of 7-month-old plants of the new cultivar as grown outdoors in 10.5-cm containers in Wezep, The Netherlands. The phenotype of the new cultivar may vary with variations in environmental, climatic, and cultural conditions, as it has not been tested under all possible environmental conditions. The color determination is in accordance with the 6$^{th}$ edition 2019 (reprint of 2015) Colour Chart of The Royal Horticultural Society, London, England, except where general color terms of ordinary dictionary significance are used.

General description:

*Blooming period*.—Summer into fall in The Netherlands.

*Plant type*.—Evergreen shrub.

*Plant habit*.—Very compact.

*Height and spread*.—Average of 15 cm in height, 20 cm spread as a 7-month-old plant grown in a container.

*Cold hardiness*.—At least to U.S.D.A. Zone 8.

*Diseases and pests*.—Moderate resistance has been observed to stem and root rot (caused by *Fusarium* sp.), no susceptibility or resistance to pests has been observed.

*Root description*.—Fibrous to slightly fleshy.

*Propagation*.—Softwood stem cuttings.

*Root development*.—Root initiation occurs in 3 weeks in summer and 6 weeks in winter, time to produce a fully rooted cutting is about 2 months.

*Growth rate*.—Moderate.

Branch description:

*Branch size*.—Average of 12.7 cm in length and 2.75 mm in diameter.

*Branch shape*.—Round.

*Branch color*.—Young; 146C, mature; a blend of 144A and 146C, internodes N186C, bark; N200B.

*Branch surface*.—Surface luster is moderately glossy.

*Branch strength*.—Strong.

*Branch aspect*.—Held in an average angle of 45°.

*Internode length*.—Average of 8 mm.

*Branching habit*.—13 main branches, 6 lateral branches per lateral branch.

Foliage description:

*Leaf shape*.—Ovate to ovate-elliptic, slightly carinate.

*Leaf division*.—Single.

*Leaf base*.—Cuneate.

*Leaf apex*.—Acute.

*Leaf venation*.—Pinnate, color upper surface; 148B, color lower surface; 144C.

*Leaf margins*.—Entire, coarsely undulate to nearly folded near the apex.

*Leaf attachment*.—Petiolate.

*Leaf arrangement*.—Opposite.

*Leaf surface*.—Both surfaces smooth, glabrous, non-rugose, upper surface moderately glossy, lower surface slightly glossy.

*Leaf color*.—Young upper surface; 143A, young lower surface; 143C, mature upper surface; 137B, mature lower surface; 146B.

*Leaf size*.—An average of 2.2 cm in length and 1.1 cm in width.

*Petioles*.—1 mm in length, 1 mm in diameter, flattened, both surfaces are smooth, glabrous, and very slightly glossy, strong, color; upper and lower surface 145A to 145B.

Flower description:

*Inflorescence type*.—Raceme.

*Inflorescence size*.—Average of 3.3 cm in height and 2.1 cm in width.

*Inflorescence lastingness*.—About 7 days, self-cleaning.

*Flower shape*.—Campanulate.

*Flower fragrance*.—None.

*Flower quantity*.—Average 55 flowers per inflorescence, 1,250 flowers per plant, 5,000 flowers and flower buds per plant.

*Flower arrangement*.—Axillary racemes.

*Flower aspect*.—Outward.

*Flower size*.—Average of 7.5 mm in height and depth, 6 mm in diameter, throat 1 mm in diameter, flower tube 3 mm in length and 2 mm in diameter.

*Peduncles*.—Strong strength, 4.4 cm in length and about 1 mm in diameter, 144B in color, held at about a 40° angle to vertical, surface is very slightly glossy and densely covered with very short glandular hairs; an average of 0.1 mm in length, color matches surface color.

*Pedicels*.—Strong, surface is matte, average of 5 mm in length and 0.5 mm in diameter, held in a 40° angle to peduncle, 144B in color.

*Flower buds*.—Narrow elliptic, 4.5 mm in length and 1.5 mm in diameter, narrow obovate-oblong in shape, surface is matte, smooth and glabrous, color; 72D, immature calyx 146B.

*Petals*.—Average 4, 1 whorl, 50% of base is fused into campanulate shape, oblong to slightly concave in shape, entire margins, apex obtuse, size; all petals 3 mm in length, of upper and lateral petals; 2.5 mm in width, dorsal lower petal 2 mm in width, both surfaces glabrous, non-rugose, and matte, color; when opening upper surface 67D, margins 67C, when opening lower surface 73D, margins 72D, when fully open upper surface 73B and 73C, when fully open lower surface 75C and 75D, upper and lower surface fading to 76D, margins and veins 76C, throat color N78D, tube outside 76B, base 155C, inside N78D, base 155C.

*Calyx*.—Rotate-shaped, average of 2.5 mm in length and 2.25 mm in diameter.

*Sepals*.—4, 2 upper, 2 lower, ovate in shape with entire margins, 2 mm in length, 2.5 mm in length, rotate, bluntly acute apex, base cuneate and fused, both surfaces glabrous, upper surface slightly glossy, lower surface slightly matte, color; when opening and fully open upper surface 143A, when opening and fully open lower surface 146D.

*Floral bracts*.—A single bract is placed below each individual flower, narrow ovate in shape, acute apex, cuneate base, 2.5 mm in length, 0.75 mm in width, both surfaces glabrous and 143B in color.

Reproductive organs:

*Gynoecium*.—Pistil; 1, 7 mm in length, stigma; 0.5 mm in diameter, club-shaped, N79B in color, style; 6.75 mm in length, 72B in color, ovary; 143A in color.

*Androecium*.—Stamens; 2, anthers; oblong in shape, 5 mm in length, 0.5 mm in width and N79C in color, filaments; 5 mm in length, 76D in color, pollen; none observed.

*Fruit and seed*.—None observed to date.

It is claimed:

1. A new and distinct cultivar of *Hebe* plant named 'Nina' as herein illustrated and described.

* * * * *